(12) United States Patent
Landers et al.

(10) Patent No.: US 12,337,069 B1
(45) Date of Patent: Jun. 24, 2025

(54) DETOXIFYING LIGHT EMITTING DEVICE AND USE THEREOF

(71) Applicant: U.S. Army Combat Capabilities Development Command, Chemical Biological Center, Apg, MD (US)

(72) Inventors: John M Landers, Riverton, NJ (US); Hui Wang, Hanover, MD (US); Christopher J Karwacki, Churchville, MD (US)

(73) Assignee: Government of the United States as Represented by the Secretary of the Army, Washington, DC (US)

( * ) Notice: Subject to any disclaimer, the term of this patent is extended or adjusted under 35 U.S.C. 154(b) by 703 days.

(21) Appl. No.: 17/720,080

(22) Filed: Apr. 13, 2022

(51) Int. Cl.
| | |
|---|---|
| *A61L 2/08* | (2006.01) |
| *A62D 3/30* | (2007.01) |
| *B01J 21/06* | (2006.01) |
| *B01J 23/42* | (2006.01) |
| *B01J 35/39* | (2024.01) |

(52) U.S. Cl.
CPC ............... *A61L 2/088* (2013.01); *A62D 3/30* (2013.01); *B01J 21/063* (2013.01); *B01J 23/42* (2013.01); *B01J 35/39* (2024.01)

(58) Field of Classification Search
CPC ............. A61L 2/088; A62D 3/30; B01J 35/39
See application file for complete search history.

(56) References Cited

U.S. PATENT DOCUMENTS

2012/0100039 A1* 4/2012 Appeaning ............. A61L 2/088
422/186.01

OTHER PUBLICATIONS

Li et al. "Efficient visible-light photocatalytic hydrogen evolution over platinum supported titanium dioxide nanocomposites coating up-conversion luminescence agent (Er3+:Y3Al5O12/Pt-TiO2)." International Journal of Hydrogen Energy 40 (2015) 2132-2140. (Year: 2015)*

Xiao et al. "2-Pyridone-functionalized Aza-BODIPY photosensitizer for imaging-guided sustainable phototherapy." Biomaterials 183 (2018) 1-9. (Year: 2018).*

Wang et al. "Photocatalytic Oxidation of Sulfur Mustard and Its Simulant on BODIPY-Incorporated Polymer Coatings and Fabrics." ACS Appl. Mater. Interfaces 10 (2018) 18771-18777. (Year: 2018).*

* cited by examiner

*Primary Examiner* — Timothy C Cleveland
(74) *Attorney, Agent, or Firm* — Ulysses J. Biffoni; Timothy M. Barlow

(57) ABSTRACT

A device is provided that can be rapidly decontaminated in response to exposure to toxic chemicals and biological materials. The device combines electroluminescence (EL) surfaces and panels with a reactive coating including a dye that acts to neutralize toxic chemical and biological materials. A current is applied to an EL display that has been coated with a fluorescent dye. The dye in turns converts nearby ambient oxygen to the more reactive singlet oxygen form that is responsible for the decontamination of toxic chemicals and agents in proximity to the device. Potential uses of the reactive decontamination device include surface panels of vehicles, exterior and interior surfaces of buildings, furniture, wands, and flexible surfaces such as tarps for tents, as well as fabrics and textiles, both woven and non-woven.

14 Claims, 5 Drawing Sheets

DETOXIFYING LIGHT EMITTING DEVICE AND USE THEREOF

GOVERNMENT INTEREST

The invention described herein may be manufactured, used, and/or licensed by or for the United States Government.

FIELD OF THE INVENTION

The present invention relates in general to the technical field of chemical agent decontamination, and in particular to self-decontaminating surfaces formed with a light emitting surface treated with a surface coating that generates singlet oxygen from ambient oxygen that can decontaminate chemical agents including a chemical warfare agent (CWA), toxic industrial chemicals (TIC), biological agents or combination thereof.

BACKGROUND OF THE INVENTION

Combat vehicles, physical enclosures, and personal protective equipment (PPE) including wearable garments are required in an environment when exposure to toxic agents such as a chemical warfare agent (CWA) is to be expected. Chemical warfare agents (CWAs) and related toxic chemicals present a lethal threat upon exposure. These chemicals can be dispensed either through a gaseous, vapor, or liquid form, and contaminate surfaces upon contact. Lethality can occur through different pathways and may include inhalation or being absorbed through the skin.

CWAs commonly encountered include bis(2-chloroethyl) sulfide, also known as HD or mustard gas, which is a powerful vesicant that causes large blisters on the exposed skin, eyes, and lungs. 1 Pinacolyl methylphosphonofluoridate, which is also known as Soman or GD, and O-ethyl S-(2-diisopropylamino) ethyl methylphosphonothiolate, known as VX, are nerve agents that represents a class of organophosphorus compounds (OPs) that inhibit acetylcholinesterase (AChE). The inhibition of AChE causes neuromuscular paralysis, which if left untreated can lead to death within minutes of exposure. Despite an international ban, chemical warfare agents continue to be a deployed in combat areas and in terrorist attacks.2, 3

In addition to these chemical agents, CWA simulants that are similar in molecular structure and are used for screening also pose a threat. A class of simulants illustratively includes 2-chloroethylphenl sulfide (CEPS) and 2-chloroethylethyl sulfide (CEES), both simulants for HD (mustard gas). Toxic industrial chemicals (TIC) are an additional class of chemicals that pose a lethal threat. Examples of pesticides illustratively include parathion, paraoxon diazinon, and malathion. Efforts are thus needed to provide protection for people and decontaminate surfaces that may come in contact with or are exposed to these dangerous chemicals. In addition to military personnel, the use of functional protective clothing and reactive surfaces against toxic chemicals are recommended for first responders such as firefighters and police officers, researchers and scientists, and workers in the pesticide industry. For instance, opioids that include but are not limited to fentanyl, carfentanil, sufentanil and remifentanil currently pose a threat to first responders. These opioids can undergo oxidation at the pyridine ring which produces the metabolite product, which is commonly less toxic than the original opioid prior to oxidation. Opioids that include but are not limited to fentanyl, carfentanil, sufentanil and remifentanil can be dosed intravenous, inhaled or absorbed by the skin. While the precise amount of opioid that will cause an overdose is unknown and varies person to person, it is estimated that 2 mg of fentanyl is a lethal dose for most people. The more potent opioids such as carfentanil pose an even greater risk upon exposure as they require lesser quantities compared to fentanyl to cause a lethal dose. This has put persons at risk of overdosing that take these opioids by legal or illegal means, but may also include aforementioned persons such as first responders. These first responders may come in contact with these opioids when responding to someone who has or in the process of an opioid overdose. Moreover, the possible deployment of these opioids by terrorist organizations in both combat and civilian areas can put military personnel and the general public at risk.

In addition to chemical threats such as CWA, TIC and the class of opioids, biological entities such as viruses and bacteria pose a threat. This threat can be either through natural mammal translation of a virus from an animal to human and sequential spread of the biological entity or from the intentional laboratory development by humans. Furthermore, whether the biological entity naturally evolves, or is manmade, both can be deployed by nefarious state actors or terrorist organizations. The threat of the spread and contamination of biological entities that can cause harm has been highlighted by the ongoing COVID-19 pandemic.

The first decontaminants used for chemical warfare agents were bleach powders of varying formulations.4 Even though bleach is quite effective in decontamination, bleach has many drawbacks: (1) fresh samples must be prepared due to loss of activity over time; (2) a large quantity of bleach is required for decontamination; and (3) bleach poses an environmental concern as it is corrosive. More recent decontamination solutions also possess several disadvantages, best illustrated with the decontamination solution DS2 utilized by the U.S Army. Comprised of NaOH, ethylene glycol monomethyl ether and diethylenetriamine, DS2 solution is effective against CWAs, but with the disadvantage that DS2 solution is flammable, toxic, corrosive and can release toxic by-products. Since then, materials have emerged in the search of new decontaminants for sulfur mustard, such as hydrogen peroxides,5-8 metal oxides,9-12 polyoxometalates,13,14 and metal-organic frameworks (MOFs).15-18 Despite significant improvements, many of these materials or methods are limited to decontamination in solutions and cannot be directly applied on the battlefield for real-time protection.

Current U.S. military doctrine requires a time-consuming process of wiping down an exposed vehicle or surface with sorbent powder mitts, followed by application of a water-based decontamination solution. This represents a logistical burden for instances where resources are scarce and a vehicle is far removed from a decontamination site. Due to the unpredictable nature of CWA events, strategies that enable the warfighter to immediately decontaminate upon exposure and alleviate the spread of contamination are warranted. Wang et al.19 recently demonstrated the use of a waterless BODIPY (boron-dipyrromethene) photosensitizer dye which when irradiated with a light emitting diode (LED) light source, generates singlet oxygen, which is referred synonymously as dioxygen (singlet) or dioxidene, and can rapidly and selectively decontaminate the CWA mustard gas (HD) into a benign sulfoxide. While this has proved to be effective considerable labor is still required to apply the dye and irradiate the target surfaces. Furthermore, the COVID-19 pandemic has shown the need for surfaces that can self-decontaminate biological entities. Self-decontaminating surfaces have been produced capable of inactivating biological entities and may include composites that incorporate antimicrobial nanoparticles (copper, silver, zinc, titanium dioxide), polyelectrolyte coatings, photosensitizer materials, or combination thereof. In the case of photosensitizer materials, an external light source is required to irradiate the surface coating that in turn generates reactive oxygen species such as singlet oxygen. Viral inactivation can then proceed after the formation of the singlet oxygen species.

Thus, there exists a need to rapidly decontaminate surfaces that have been exposed to chemical contaminants and chemical warfare agent (CWA) or biological agents in order to prevent the spread of contamination and allow for first responders and military personnel to carry out mission-essential objectives and lifesaving activities. There further exists a need to complete a surface decontamination with limited effort so as to allow personnel to proceed with their mission.

SUMMARY OF THE INVENTION

The present invention provides a decontamination device for response to exposure to toxic agents, chemicals, opioids, and chemical warfare agents (CWA), simulants, and biological entities such as bacteria or viruses.

A light emitting device emits wavelengths of light to excite a dye in a coating to emit singlet oxygen upon irradiation by the light emitting device. The light emitting device illustratively includes an electroluminescent (EL) device or a light emitting diode array. The coating in some inventive embodiments has an overlayer that is opaque and porous to the diffusion of singlet oxygen therethrough. The device can be in the form of a panel or film that can be attached to an object that is at risk of exposure to a toxin, such as a CWA.

A method of decontamination of a toxin is also provided. The method includes a light emitting device being energized in optical communication with a material that emits singlet oxygen. The singlet oxygen is brought into proximity to the toxin. Decontamination occurs after allowing sufficient time for the singlet oxygen to react with the toxin to achieve decontamination.

BRIEF DESCRIPTION OF THE DRAWINGS

The present invention is further detailed with respect to the following figures that depict various aspects of the present invention.

DETAILED DESCRIPTION OF THE PREFERRED EMBODIMENTS

Figure 1:
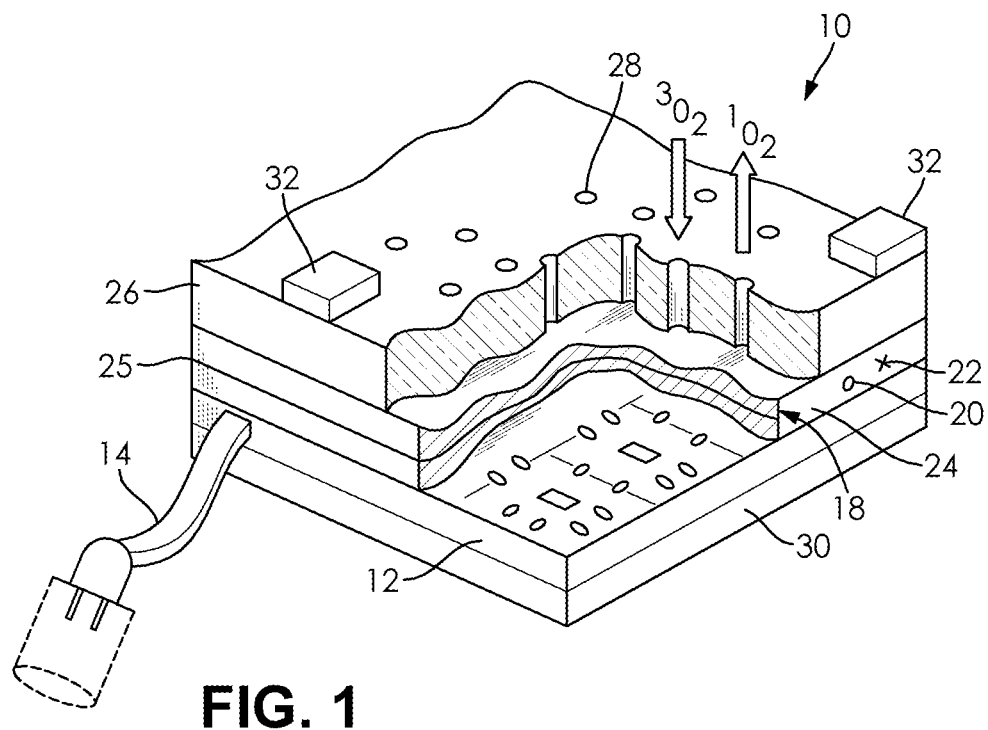
FIG. 1 is a partial cutaway view of a first embodiment of an inventive device in which relative sizes are varied for visual clarity.

The present invention has utility as a device that can rapidly decontaminate a toxin. Embodiments of the inventive device include a light emitting device of an electroluminescence (EL) panel, a light emitting diode array, or a combination thereof. Light emission from the light emitting device stimulates a reactive coating to decontaminate toxic agents, chemicals, or CWA through generation of singlet oxygen. Potential applications for embodiments of the present invention include surface panels of vehicles, exterior and interior surfaces of buildings, furniture, flexible surfaces such as tarps for tents, as well as fabrics and textiles, both woven and non-woven.

As used herein, a toxin is defined as a chemical warfare agent (CWA), a CWA simulant, a Toxic Industrial Chemical (TIC as defined by the OSHA Guide circa May 2021), an opioid, or other hazardous chemical.

Embodiments of the present invention provide a way to rapidly decontaminate surfaces by applying an electrical current to the light emitting device. The light emission from the light emitting device is in optical communication with a fluorescent dye stimulated by the emissions from the light emitting device. The dye under such conditions converts ambient atmospheric oxygen into singlet oxygen. Singlet oxygen diffuses from the dye and into contact with a toxin to reactively decontaminate the toxin. The dye is present as a coating on the light emitting device or is remotely excited by way of an optical fiber.

In certain embodiments of the present invention is provided in the form of a panel that is either rigid or sufficiently flexible to conform to a target surface. The light emitting device is selectively energized to initiate decontamination of a toxin in response to a contamination event or pre-emptively relative to a toxin exposure.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

A dye operative in the present invention is single compound or multicomponent catalytically active species effective to decontaminate a toxin, such as a CWA. A dye operative in the present invention illustratively include 4,4-difluoro-4-bora-3a,4a-diaza-s-indacene (BODIPY), 1,3,5,7-tetramethyl-8-phenyl-substituted BODIPY (BODPIY-H); 1,3,5,7-tetramethyl-2,6-ido-8-phenyl-substituted BODIPY (BODPIY-I); 1,3,5,7-tetramethyl-2,6-sulfonyl-8-phenyl-substituted BODIPY (BODPIY-SO3); ethyl 2-(4-methoxyphenyl)-4H-thieno[3,2-b]pyrrole-5-carboxylate; 2-(4-methoxyphenyl)-4H-thieno[3,2-b]pyrrole-5-carboxylic acid; 2,8-Di (4-methoxyphenyl)-11-trifluoromethyl-dithieno[2,3-b]-[3,2-0-5,5-difluoro-5-bora-3a,4a-dithio-s-indacene; 3,7-Dibromo-2,8-di (4-methoxyphenyl)-11-trifluoromethyl-difuro[2,3-b]-[3,2-g]-5,5-difluoro-5-bora-3a,4a-diaza-s-indacene; 3,7-Dibromo-2,8-di (4-methoxyphenyl)-11-trifluoromethyl-dithieno[2,3-b]-[3,2-g]-5,5-difluoro-5-bora-3a,4a-diaza-s-indacene; 3,7,9,12-Tetrabromo-2,8-di (4-methoxyphenyl)-11-trifluoromethyl-difuro[2,3-13]-[3,2-g]-5,5-diflauro-5-hora-3a,4a-diaza-s-indacene; Rose Bengal, fluorescein; eosin blue; Methylene blue; erythrosin blue; porphyrins; phthalocyanines; napthalocyanines; chlorines; bacterichlorines; texaphyrines; sqaurylium dyes as detailed in P. F. Santos, et al. "Singlet Oxygen Generation Ability Of Squarylium Cyanine Dyes, J. of Photochem. and Photobio. A: Chemistry, 160 (3), 2003, pp 159-161; and combinations thereof. In some inventive embodiments, an inventive device includes BODIPY dyes to take advantage of thermal and photochemical stabilities, and high molar absorptivities in the visible light region,20 and readily tunable molecular structures,21 allowing their photophysical and electrochemical properties to be conveniently optimized, and long-lived triplet excited states and high 1O2 quantum yields. Thermal stabilities includes storage stability at temperatures of from-40 to 40 C.

In specific inventive embodiments, 2-Pyridone-functionalized Aza-BODIPY is present in the device. Multifunctional water-soluble BODIPY nanoparticles (NPs), have high photothermal conversion efficiency of 35.7% and provide excellent singlet oxygen (1O2) generation ability. The reversible transformation between 2-pyridone moiety and its endoperoxide form endows BDY with continuous 1O2 generation ability under illumination and non-illumination conditions.22

An inventive device has the attribute that the surface coating used in inventive embodiments described herein is non-stoichiometric: in that with an applied electrical current to the light emitting device, the BODIPY coating continues to generate singlet oxygen from ambient oxygen that can decontaminate a toxin such as a CWA. Therefore, the useful lifetime of the inventive surfaces is not limited. In contrast, self-decontaminating surfaces found in the prior art rely on passive decontamination in that the surface tends to be coated with a material that reacts with limited turn over frequencies resulting from the stoichiometric nature of the active catalyst in the composition. This means that for every individual chemical reaction the active material in the coating is transformed to a product that may no longer react for decontamination resulting in a finite operation lifetime proportional to the amount of dye present.

Embodiments of the inventive decontamination panels detoxify toxins that include with CWAs from classes that illustratively include but are not limited to G, V, and H class agents such as sulfur mustard (HD), VX, tabun (GA), and sarin (GB); CWA simulants that illustratively include 2-chloroethyl ethyl sulfide (2-CEES), dimethyl methylphosphonate (DMMP), dimethyl chlorophosphate (DMCP), diisopropyl methylphosphonate (DIMP), methyl dichlorophosphate (MDCP), and difluorphosphate (DFP); hazardous chemicals that illustratively include ammonia, hydrogen chloride, sulfur dioxide, hydrogen sulfide, and cyanogen chloride. Opioids may also be oxidized by embodiments of the inventive surface composites illustratively including but not limited to fentanyl, carefentanil, sufentanil, and remifentanil.

An exemplary reaction scheme of the present invention based on a blue light emission is provided in equation (a) for detoxification of HD using the dye BODPIY-H:

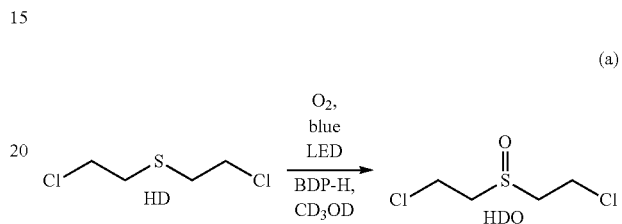

(a)

An embodiment of an inventive device is depicted as a partial cutaway generally at 10 in FIG. 1. The relative dimensions of the layers of the device 10 are distorted for visual clarity. The device 10 includes a light emitted device 12. The light emitting device 12 as shown in FIG. 1 is an electroluminescent (EL) sheet and also includes a light emitting diode (LED) array, as is shown with respect to FIG. 2A. It is appreciated that the light emitted device 12 is either a flexible sheet that is conformable to a substrate or is a free standing. Substrates operative herein illustratively include surface panels of vehicles, exterior and interior surfaces of buildings, furniture, flexible surfaces such as tarps for tents, as well as fabrics and textiles. A power source connector 14 provides electrical current sufficient to energize the light emitting device 12 to emit light of at least one preselected wavelength. Typical wavelengths suitable for dye stimulation range from 280 to 780 nm. The power source connector 14 is coupled to a power source 16 such as a battery, line power, solar cell, dynamo that is either hand or machine operated, or a vehicle power system.

In inventive embodiments, a coating 18 overlies the light emitting device 12. The coating 18 contains one or more of the aforementioned dyes, as shown schematically at 20. In some inventive embodiments, the coating 18 also includes a photoactive catalyst, as shown schematically at 22. A photoactive catalyst 22 operative herein illustratively includes titania supporting PtEr particulate, or a combination thereof. The coating 18 in some embodiments includes a resin matrix 24 in which the dye 20, and the photocatalyst 22, if present, are encapsulated. The resin matrix 24 illustratively includes polyimide, polystyrene, polydimethylsiloxane, polyurethane, and latex, a random copolymer, or a block copolymer in which any of the aforementioned comprise at least 50 percent by mole fraction of the copolymer. Copolymers operative herein illustratively include styrene-butadiene-styrene (SBS), styrene-isoprene-styrene (SIS), styrene-ethylene-butadiene-styrene (SEBS), and styrene-ethylene-propylene-styrene (SEPS), and combinations thereof.

In operation, upon energizing the light emitting device 12 to emit one or more wavelengths to stimulate the dye 20 and photocatalyst 22, if present, ambient atmospheric oxygen in contact with the coating 18 is converted in part to singlet oxygen that is able to diffuse from the coating 18 and react with proximal toxins. Singlet oxygen has a lifetime of approximately 3 seconds at Standard Temperature and Pressure and a root mean square (rms) diffusion distance of 2 centimeters. These are defined as proximal herein for the purposes of detoxification. A coating 18 is readily formed by a multitude of manufacturing techniques such as layer-by-layer deposition, spraying, dipping, spin casting, or immersion of the light emitting device 12 or an intermediate layer 25 that is able to transmit wavelengths necessary to stimulate the coating 18.

In some use environments, there is a desire to not have light emission emanating from the coating 18 so as to communicate the location of the coating 18 at a distance. In such environments, the coating 18 has an opaque and porous overlayer 26 that is permeable to the singlet oxygen outward diffusion and ambient air oxygen diffusion inward. An overlayer 26 is illustratively formed of a conventionally pigmented breathable paint of limewash that typically contains 3% acrylic to promote adhesion and limit dusting, clay paint, silicate mineral paints. These allow gas transfusion yet are opaque and can be provided in any number of colors. The overlayer 26 is depicted with pores 28 through which the diffusion occurs.

In some use settings, an inventive device 10 is adhered to a substrate that has the possibility to be exposed to a toxin, such an exterior surface. In some pre-emptive placement embodiments, a backing 30 is provided that adhesively secures the device 10 to a substrate. In some use settings, where an inventive device 10 is applied to a substrate after a toxin exposure, adhesive pads 32 are provided to direct the singlet oxygen emitted onto the toxin contaminated substrate, independent of whether the overlayer 26 is present.

Figure 2A:
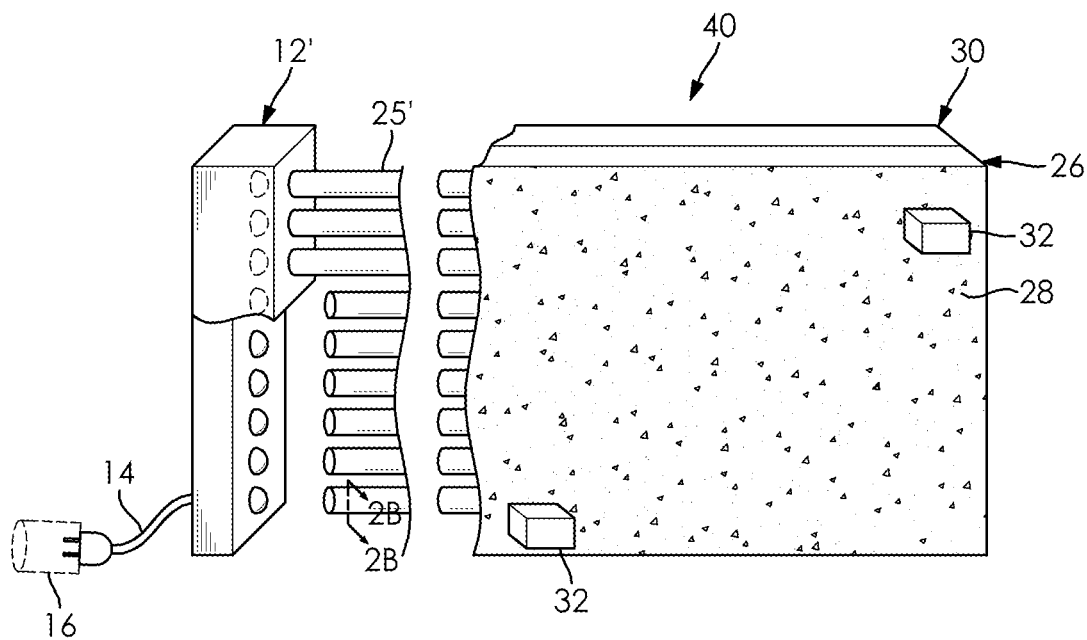
FIG. 2A is a partial cutaway view of a second embodiment of an inventive device in which relative sizes are varied for visual clarity.
Figure 2B:
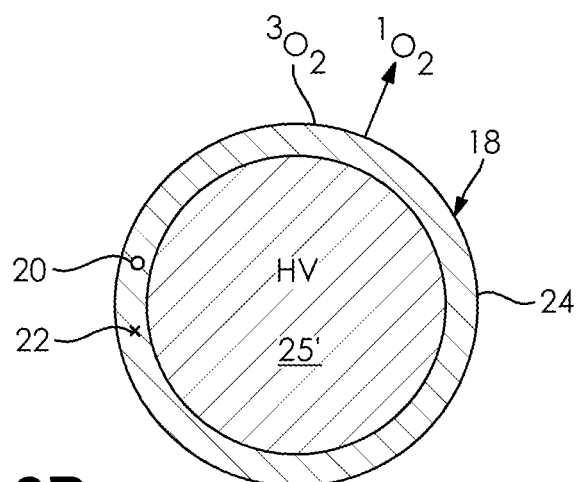
FIG. 2B is a cross-sectional view of a fiber along the plane 2B-2B' of FIG. 2A.

Another inventive embodiment is depicted in FIGS. 2A and 2B generally at 40 where like numerals have the aforementioned meanings ascribed thereto with respect to FIG. 1. A light emitting device 12' is an LED array and is shown in partial cutaway view in FIG. 2A. LED arrays in linear or two-dimensional arrays are commercially available with the wavelength emissions required herein to induce singlet oxygen generation through dye stimulation, alone or in combination with a photocatalyst. The light emitting device 12' is in optical communication with an intermediate layer 25' in the form of optical fibers positioned to transmit the light along the length of the fibers to stimulate dye 20 and photocatalyst 22, if present, in a coating 18 formed as a sizing around the fibers of the intermediate layer 25' to convert triplet oxygen to single oxygen, as best seen in FIG. 2B. Optical fibers operative herein are typically formed of glass or quartz with material selection largely dictated by the required wavelength transmissivity. FIG. 2B is a cross sectional view of a single fiber of the intermediate layer 25' in the plane 2B-2B'. The device 40 is depicted in the form of a ribbon yet it should be appreciated that complex two or three-dimensional shapes are readily formed such as an overlay for an entire vehicle.

Figure 3A:
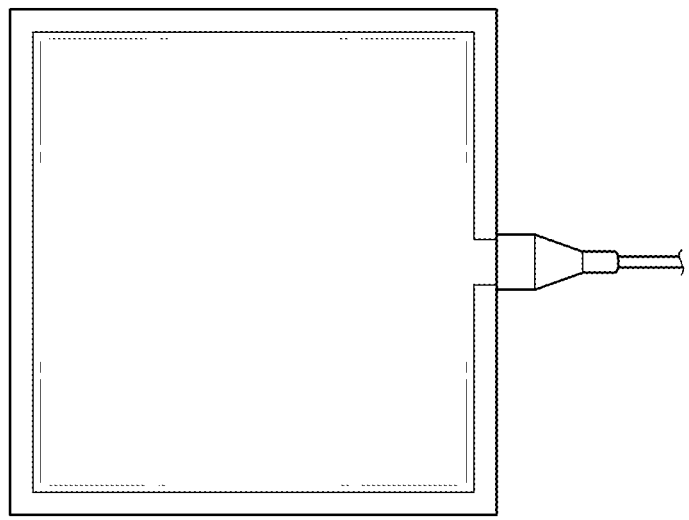
FIG. 3A depicts an electroluminescence (EL) panel as the light emitting device in an "off state" with no current applied and no coating thereon.
Figure 3B:
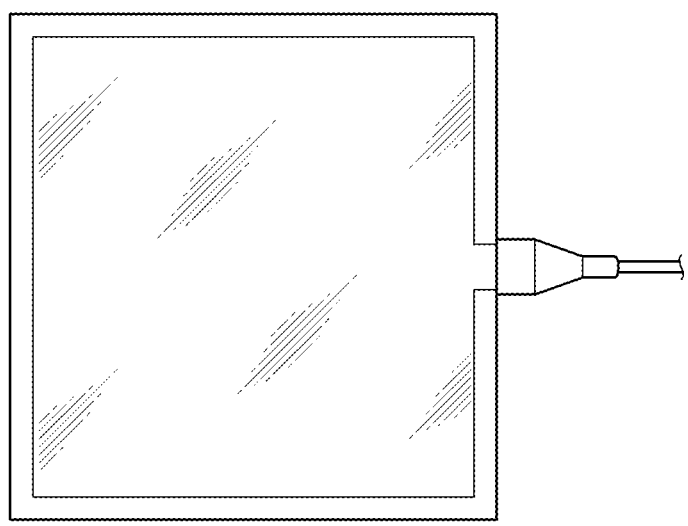
FIG. 3B depicts the EL panel of FIG. 3A in an "on state" with an electric current applied.

FIG. 3A illustrates an uncoated panel. FIG. 3B illustrates the panel with the EL active.

Figure 4A:
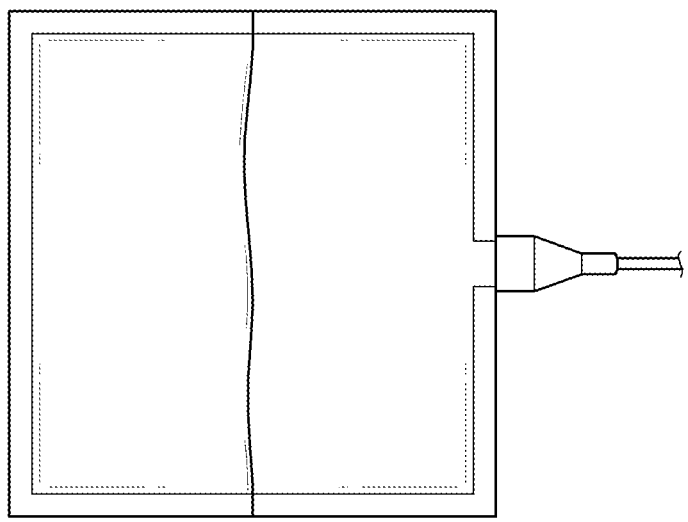
FIG. 4A depicts the EL panel of FIG. 3A with the left side of the panel coated with BODIPY in an "off state" in accordance with embodiments of the invention.
Figure 4B:
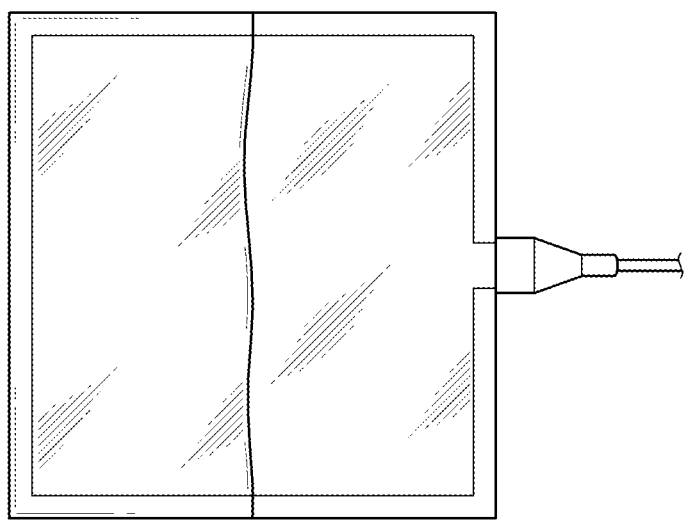
FIG. 4B depicts the BODIPY coated panel of FIG. 4A in an "on state" in accordance with embodiments of the invention.

FIG. 4A illustrates the EL panel of FIG. 3A with the left side of the panel coated with BODIPY in an "off state". FIG. 4B is a photograph of the BODIPY coated panel of FIG. 4A in an on-state. The coating material is able to react with methanol as a model for mustard gas.

Figure 5:
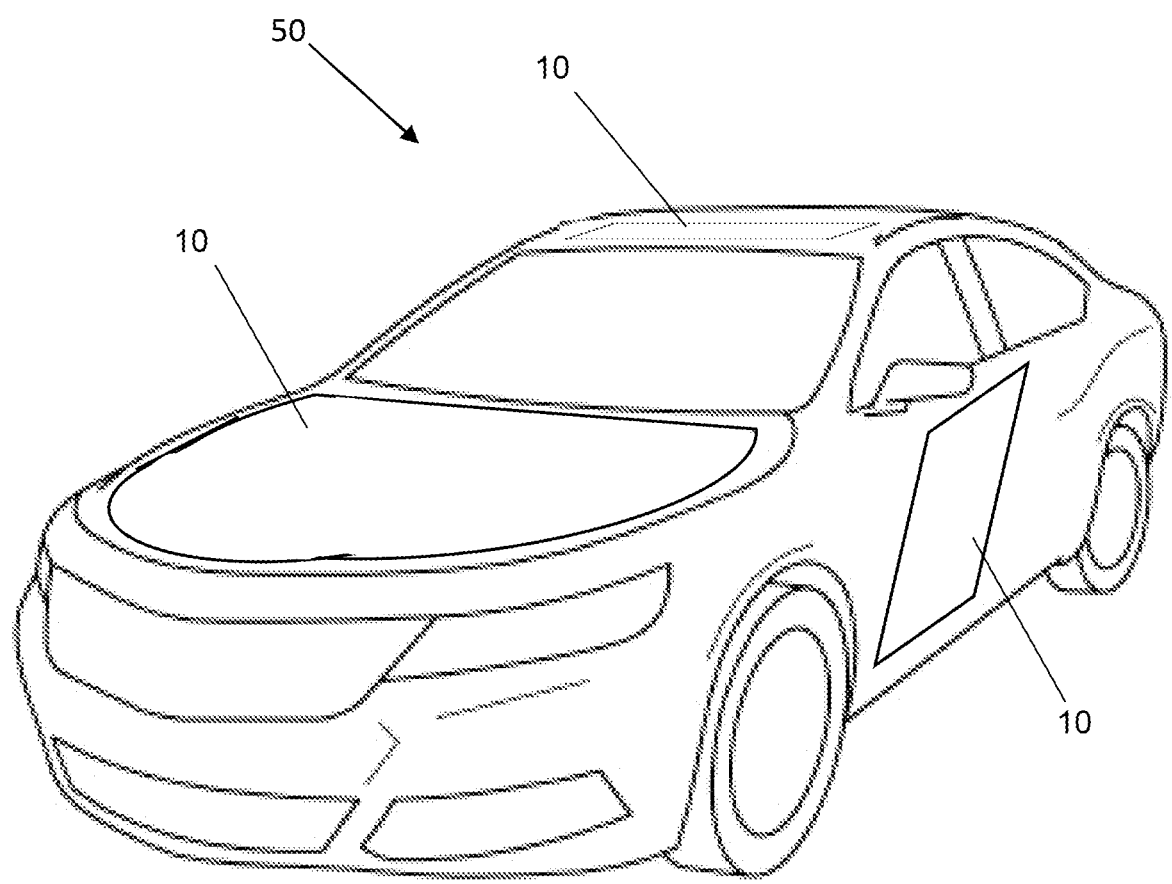
FIG. 5 illustrates a vehicle with the inventive decontamination EL panels affixed to one or more surfaces of a vehicle in accordance with embodiments of the invention.

FIG. 5 illustrates a vehicle 50 with the inventive devices 10 affixed to one or more surfaces of the vehicle. It is appreciated vehicles may include first responder vehicles illustratively including ambulances, fire trucks, and patrol cars, as well as military transport and combat vehicles. It is further appreciated that mass transportation vehicles and trains may also be equipped with embodiments of the inventive device 10'. The devices 10 may be formed as a flexible decal with an adhesive backing that can be affixed to the surface of a vehicle.

Figure 6:
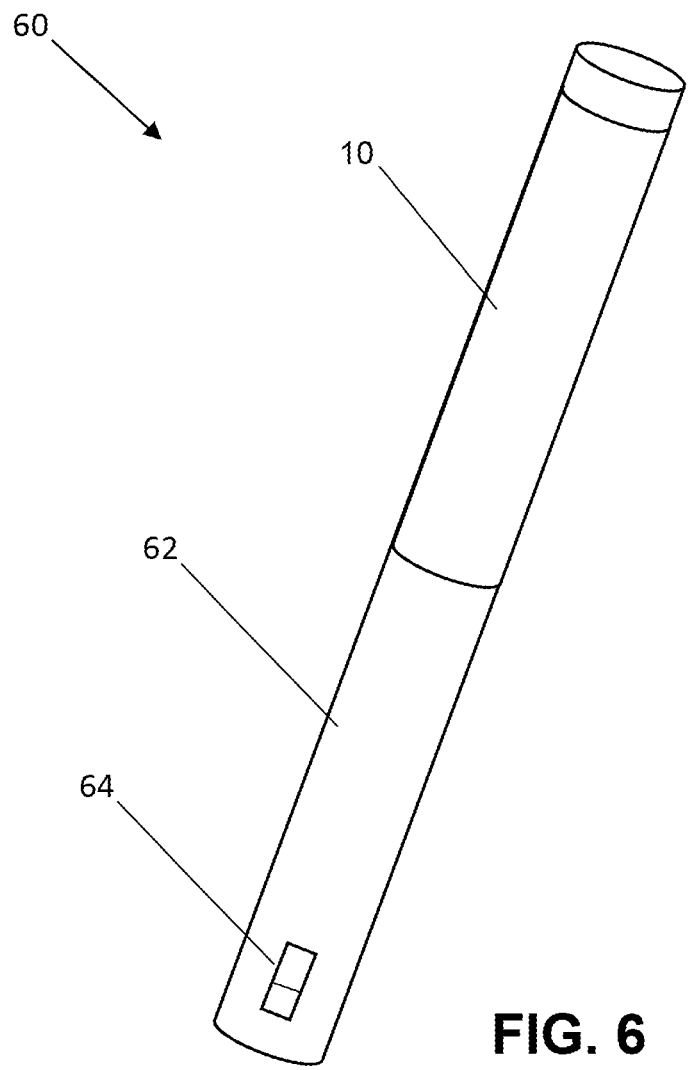
FIG. 6 illustrates a decontamination device in the form of a wand in accordance with embodiments of the invention.

FIG. 6 illustrates a wand 60 having a handle portion 62 with an on/off switch 64 with a flexible device 10 provided as a decal wrapped about the upper circumference of the wand 60. A user waves the wand 60 over a toxin contaminated area with switch 64 in the "on" position to diffuse singlet oxygen from the dye to neutralize the toxin.

Publications mentioned in the specification are indicative of the levels of those skilled in the art to which the invention pertains. These applications and publications are incorporated herein by reference to the same extent as if each individual application or publication was specifically and individually incorporated herein by reference.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

REFERENCES

1. Fitzgerald, G. J. *American journal of public health* 2008, 98, (4), 611-625,
2. Fassihi, F. *The Wall Street Journal* 2016.
3. Khadder, K.; Elwazer, S.; Roberts, E.; Kourdi, E.; Qiblawi, T., Suspected Gas Attack in Syria Reportedly Kills Dozens. CNN: 2017.
4. Yang, Y. C.; Baker, J. A.; Ward, J. R. *Chemical Reviews* 1992, 92, (8), 1729-1743.
5. Wagner, G. W.; Yang, Y.-C. *Industrial & engineering chemistry research* 2002, 41, (8), 1925-1928.
6. Wagner, G. W.; Procell, L. R.; Sorrick, D. C.; Lawson, G. E.; Wells, C. M.; Reynolds, C. M.; Ringelberg, D. B.; Foley, K. L.; Lumetta, G. J.; Blanchard Jr, D. L. *Industrial & Engineering Chemistry Research* 2010, 49, (7), 3099-3105.
7. Picard, B.; Gouilleux, B.; Lebleu, T.; Maddaluno, J.; Chataigner, I.; Penhoat, M.; Felpin, F. X.; Giraudeau, P.; Legros, J. *Angewandte Chemie* 2017, 129, (26), 7676-7680.
8. Wagner, G. W.; Procell, L. R.; Yang, Y.-C.; Bunton, C. A., Molybdate/peroxide microemulsions useful for decontamination of chemical warfare agents. U.S. Pat. No. 6,723,891 B1.
9. Wagner, G. W.; Koper, O. B.; Lucas, E.; Decker, S.; Klabunde, K. J. *The Journal of Physical Chemistry B* 2000, 104, (21), 5118-5123.
10. Wagner, G. W.; Chen, Q.; Wu, Y. *The Journal of Physical Chemistry C* 2008, 112, (31), 11901-11906.
11. Panayotov, D.; Paul, D.; Yates, J. *The Journal of Physical Chemistry B* 2003, 107, (38), 10571-10575.
12. Bandosz, T. J.; Laskoski, M.; Mahle, J.; Mogilevsky, G.; Peterson, G. W.; Rossin, J. A.; Wagner, G. W. *The Journal of Physical Chemistry C* 2012, 116, (21), 11606-11614.

13. Gall, R. D.; Faraj, M.; Hill, C. L. *Inorganic Chemistry* 1994, 33, (22), 5015-5021.
14. Okun, N. M.; Anderson, T. M.; Hill, C. L. *Journal of Molecular Catalysis A: Chemical* 2003, 197, (1-2), 283-290.
15. DeCoste, J. B.; Peterson, G. W. *Chemical reviews* 2014, 114, (11), 5695-5727.
16. Liu, Y.; Howarth, A. J.; Vermeulen, N. A.; Moon, S.-Y.; Hupp, J. T.; Farha, O. K. *Coordination Chemistry Reviews* 2017, 346, 101-111.
17. Liu, Y.; Howarth, A. J.; Hupp, J. T.; Farha, O. K. *Angewandte Chemie* 2015, 127, (31), 9129-9133.
18. Atilgan, A.; Islamoglu, T.; Howarth, A. J.; Hupp, J. T.; Farha, O. K. *ACS applied materials & interfaces* 2017, 9, (29), 24555-24560.
19. Wang, H.; Wagner, G. W.; Lu, A. X.; Nguyen, D. L.; Buchanan, J. H.; McNutt, P. M.; Karwacki, C. J. ACS applied materials & interfaces 2018.
20. Yogo, T.; Urano, Y.; Ishitsuka, Y.; Maniwa, F.; Nagano, T. *Journal of the American Chemical Society* 2005, 127, (35), 12162-12163.
21. Loudet, A.; Burgess, K. *Chemical reviews* 2007, 107, (11), 4891-4932.
22. Xiao et al. *Biomaterials*, Elsevier, Volume 183, November 2018, Pages 1-9.

The invention claimed is:

1. A decontamination device, comprising:
a light emitting device;
a coating including a dye on said light emitting device and in optical communication with said light emitting device, wherein said coating converts ambient air oxygen into singlet oxygen upon irradiation by said light emitting device; and
an opaque and porous overlayer on said coating, said overlayer being permeable to the singlet oxygen.

2. The decontamination device of claim 1, wherein said dye is a boron-dipyrromethene.

3. The decontamination device of claim 1, wherein said dye is 2-pyridone-functionalized aza-boron-dipyrromethene.

4. The decontamination device of claim 1, wherein said coating further includes a photocatalyst.

5. The decontamination device of claim 4, wherein said photocatalyst comprises titania supporting PtEr particulate.

6. The decontamination device of claim 1, wherein said dye is one or more of 4,4-difluoro-4-bora-3a,4a-diaza-s-indacene (BODIPY); 1,3,5, 7-tetramethyl-8-phenyl-substituted BODIPY (BODPIY-H); 1,3,5,7-tetramethyl-2,6-ido-8-phenyl-substituted BODIPY (BODPIY-I); 1,3,5,7-tetramethyl-2,6-sulfonyl-8-phenyl-substituted BODIPY (BODPIY-SO3); or ethyl 2-(4-methoxyphenyl)-4H-thieno[3,2-b]pyrrole-5-carboxylate; 2-(4-methoxyphenyl)-4H-thieno[3,2-b]pyrrole-5-carboxylic acid.

7. The decontamination device of claim 1, wherein said coating comprises a resin matrix encapsulating said dye.

8. The decontamination device of claim 7, wherein said resin matrix is polyimide, polystyrene, polydimethylsiloxane, polyurethane, latex, a random copolymer, or a block copolymer in which any of the aforementioned comprise at least 50 percent by mole fraction of the copolymer.

9. The decontamination device of claim 1, wherein said light emitting device is an electroluminescence (EL) display or an array of light emitting diodes (LEDs).

10. The decontamination device of claim 1, wherein said light emitting device and said coating are conformable to a substrate or surface.

11. The decontamination device of claim 1, further comprising a backing joined to said light emitting device opposite said coating.

12. The decontamination device of claim 1, further comprising adhesive pads attached to said coating or said opaque and porous overlayer.

13. The decontamination device of claim 1, wherein said light emitting device emits at least one wavelength in the range of 280 and 780 nm.

14. The decontamination device of claim 1, wherein said decontamination device is affixed to or forms the surface panels of vehicles, exterior and interior surfaces of buildings, furniture, wands, and flexible surfaces such as tarps, tents, fabrics and textiles.

* * * * *